US009377336B2

(12) United States Patent　　　　　　　　　(10) Patent No.: US 9,377,336 B2
Boschi et al.　　　　　　　　　　　　　　　　(45) Date of Patent: Jun. 28, 2016

(54) APPARATUS AND METHOD FOR MEASURING THE FLOW-RATE OF DIFFERENT FLUIDS PRESENT IN MULTIPHASE STREAMS

(75) Inventors: Stefano Boschi, Gorgonzola (IT); Paolo Andreussi, Pisa (IT)

(73) Assignee: ENI S.P.A. (IT)

( * ) Notice: Subject to any disclaimer, the term of this patent is extended or adjusted under 35 U.S.C. 154(b) by 100 days.

(21) Appl. No.: 14/112,002

(22) PCT Filed: Apr. 18, 2012

(86) PCT No.: PCT/IB2012/051939
§ 371 (c)(1),
(2), (4) Date: Nov. 14, 2013

(87) PCT Pub. No.: WO2012/143866
PCT Pub. Date: Oct. 26, 2012

(65) Prior Publication Data
US 2014/0060205 A1　　Mar. 6, 2014

(30) Foreign Application Priority Data

Apr. 19, 2011　(IT) .............................. MI2011A0670

(51) Int. Cl.
*G01F 1/74*　　(2006.01)
*G01F 1/36*　　(2006.01)
(Continued)

(52) U.S. Cl.
CPC . *G01F 1/74* (2013.01); *E21B 47/10* (2013.01); *G01F 1/36* (2013.01); *G01F 15/08* (2013.01); *G01N 33/2823* (2013.01); *G01F 1/72* (2013.01)

(58) Field of Classification Search
CPC .............. G01F 1/36; G01F 1/72; G01F 15/08
See application file for complete search history.

(56) References Cited

U.S. PATENT DOCUMENTS 5,535,632 A * 7/1996 Kolpak ..................... G01F 1/74
　　　　　　　　　　　　　　　　　　　　　73/200
5,591,922 A * 1/1997 Segeral ..................... G01F 1/36
　　　　　　　　　　　　　　　　　　　　　73/861.04

(Continued)

FOREIGN PATENT DOCUMENTS

WO　　2006048418 A1　　5/2006
WO　　2011039593 A1　　4/2011

*Primary Examiner* — Lisa Caputo
*Assistant Examiner* — Tran M. Tran
(74) *Attorney, Agent, or Firm* — Tarolli, Sundheim, Covell & Tummino LLP

(57) ABSTRACT

The present invention relates to an apparatus and method for measuring the flow-rate of different fluids present in a plurality of distinct multiphase streams (C), in transit, each through a respective main flow pipe (2). The apparatus (1) comprises a measuring unit (3) for each pipe (2). Each measuring unit (3) comprises a sampling device (4). Each measuring unit (3) comprises first and second measuring means (5) of the differential pressure type situated downstream of the respective sampling device (4). The apparatus (1) comprises a phase separator (8) associated with the measuring unit (3). The apparatus (1) comprises selection means (18) interposed between the measuring unit (3) and the separator (8) for putting the latter in communication with one of the sampling devices (4) envisaged. The apparatus (1) comprises third measuring means (12) associated with the separator (8) for measuring the outgoing flow-rates of the different fluids separated and data processing means suitable for receiving and processing the data revealed by the measuring devices (5, 7, 12).

6 Claims, 1 Drawing Sheet

(51) Int. Cl.
   *G01F 15/08* (2006.01)
   *G01N 33/28* (2006.01)
   *E21B 47/10* (2012.01)
   *G01F 1/72* (2006.01)

(56) References Cited

U.S. PATENT DOCUMENTS

| | | | | |
|---|---|---|---|---|
| 5,654,502 A | * | 8/1997 | Dutton | G01N 33/2823 |
| | | | | 73/152.18 |
| 5,811,696 A | * | 9/1998 | Jobson | G01N 1/20 |
| | | | | 73/863.03 |
| 5,894,080 A | * | 4/1999 | Dybdahl | E21B 49/086 |
| | | | | 73/1.16 |
| 6,041,668 A | * | 3/2000 | Guieze | G01N 1/2247 |
| | | | | 73/863.03 |
| 6,062,092 A | * | 5/2000 | Weaver | G01N 1/2247 |
| | | | | 73/863.03 |
| 6,546,809 B1 | * | 4/2003 | Andreussi | 73/861.04 |
| 7,474,969 B2 | * | 1/2009 | Poulisse | E21B 47/10 |
| | | | | 166/250.01 |
| 7,717,000 B2 | * | 5/2010 | Xie | B01F 5/0682 |
| | | | | 73/863.03 |
| 7,942,065 B2 | * | 5/2011 | Xie | G01F 15/02 |
| | | | | 73/861.04 |
| 8,446,561 B2 | * | 5/2013 | Kramer | G03F 7/70341 |
| | | | | 355/30 |
| 8,516,900 B2 | * | 8/2013 | Pihlaja | G01F 1/74 |
| | | | | 73/861.04 |
| 8,606,531 B2 | * | 12/2013 | Pinguet | G01F 1/46 |
| | | | | 702/24 |
| 8,770,040 B2 | * | 7/2014 | Boschi et al. | 73/861.04 |
| 8,869,627 B2 | * | 10/2014 | Al-Hadhrami | G01F 15/08 |
| | | | | 73/861.04 |

\* cited by examiner

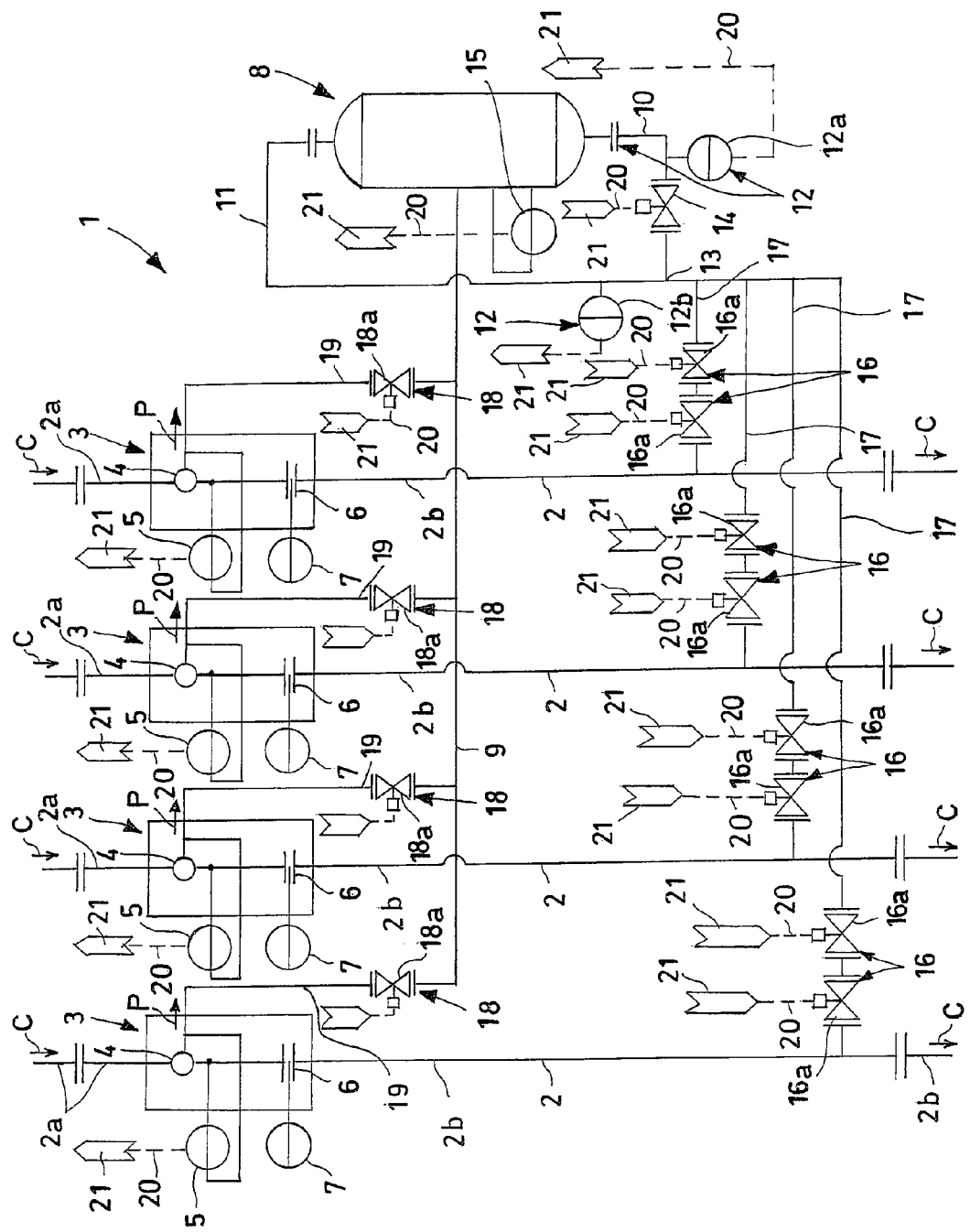

APPARATUS AND METHOD FOR MEASURING THE FLOW-RATE OF DIFFERENT FLUIDS PRESENT IN MULTIPHASE STREAMS

The present invention relates to an apparatus for measuring the flow-rates of different fluids present in a plurality of distinct multiphase streams, in transit, each through a respective main flow pipe, not forming part of said apparatus.

An object of the present invention also relates to a method for measuring the flow-rates of each phase in distinct multiphase streams, which flow in respective and different main flow pipes.

The object of the present invention is used in the oil industry and, in particular, is suitable for measuring the flow-rate of phases in multiphase streams in transit along respective flow pipes which are concentrated in off-shore or cluster on-shore platforms.

As is known, during the production of oil and gas, in a flow pipe transporting hydrocarbons, measurements are effected for determining the flow of the multiphase stream and single phases, the multiphase flow consisting of a biphasic or triphasic oil-water-gas combination.

The flow measurements of the different phases in a respective pipe transporting oil/hydrocarbons are necessary for controlling and regulating the production of hydrocarbons, and also for evaluating the water and gas content inside the multiphase flow.

In order to accurately reveal the flow of the different phases in an oil-water-gas multiphase stream, multiphase meters (MPFM) can be used, which are capable of operating in different flow regimes.

Some multiphase flow measurers are strictly linked to the oil industry, others are based on ionizing radiations, others again, are based on the use of microwaves. These instruments, however, are characterized by a significant uncertainty in the measurements.

Traditional measurement methods of multiphase fluids envisage separation of the fluid by means of a biphasic or triphasic separator and the measurement of the flow rate of the single outgoing phases.

As these separators are particularly costly, cumbersome and also heavy, normally only one triphasic separator is used for measuring various lines or flow pipes close to each other.

Through a suitable combination of valves, called manifold, any of the lines or multiphase flow pipes can be put in fluid communication with the triphasic separator, in order to effect measurements of the stream coming from a specific well, whereas all the other multiphase flow pipes remain in a production condition. The measurement effected according to this process is a non-continuous measurement of the flow-rates of the phases of the multiphase streams analyzed. In other words, this measurement is effected on samples of stream taken directly from the relative lines or multiphase flow pipes.

In addition to the manifold for communication with the separator, this system also provides a further production manifold to which all the lines or flow pipes coming from the respective wells, are sent.

Multiphase flow-rate meters which use isokinetic sampling coupled with a total flow-rate meter of the multiphase stream, are also known, as described and illustrated in the documents WO2005/031311 and WO2007/060386. The total flow-rate meter operates independently of the isokinetic sampling, allowing the liquid and gas flow-rates of the multiphase mixture to be characterized.

An apparatus and simple multiphase flow measurement method based on isokinetic sampling, capable of operating with high volumetric fractions of liquid, i.e. (LVF)>10% and in any flow regime, such as laminar, bubble, slug, and the like, are also known.

This system is generally applied for each line or flow pipe coming from the wells and effects a continuous measurement of oil, gas and water from the single well.

Although different measurement techniques of the multiphase streams have particular advantages, the Applicant has found that they are not without drawbacks and many aspects can be improved, mainly with respect to the accuracy of the measurement effected, the diversion of considerable masses of multiphase streams, the overall encumbrance of the apparatus, in addition to the overall costs of the latter.

In particular, the Applicant has found that the traditional multiphase measurement methods by the grouping of lines envisage the total collection of the flow-rate of each line. In this way, the whole multiphase flow collected is sent to the triphasic separator which must be suitably dimensioned creating significant encumbrances and costs.

Alternatively, the method of transferring the whole multiphase flow to a multiphase measuring device of the known type, is known. This method implies dimensioning the multiphase meter over the whole envelope of possible measurement ranges during the useful life for all the wells whose fluid stream must be measured by the measurer of the known type, a condition which is difficult to reach without accepting strong degradations in the measurement accuracy.

Other methods, on the other hand, envisage a continuous measurement of the multiphase flow-rates requiring a measurement system for each line envisaged. Of course, the costs and encumbrances of each system must be so multiplied by each stream line envisaged.

The main objective of the present invention is to provide an apparatus and method for measuring the flow-rate of different fluids present in a plurality of distinct multiphase streams, capable of solving the problems found in the known techniques.

An objective of the present invention is to guarantee an accurate measurement of the flow-rates of the phases of multiphase streams.

A further objective of the present invention is to allow an optimum semi-continuous measurement of multiphase streams in groupings of multiphase stream lines.

Another objective of the present invention is to reduce the flow-rates of the multiphase streams to be separated.

Yet another objective of the present invention is to simplify the measurement apparatus.

A further objective of the present invention is to reduce the overall encumbrance of the measurement apparatus.

Another objective of the present invention is to reduce the overall costs of the measurement apparatus.

The objectives specified above, and others, are substantially achieved by an apparatus and method for measuring the flow-rate of different fluids present in a plurality of distinct multiphase streams, as expressed and described in the following claims.

The description is now provided of a preferred, but not exclusive, embodiment of an apparatus and method for measuring the flow-rate of different fluids present in a plurality of distinct multiphase streams, according to the present invention. This description is effected hereunder with reference to the attached drawing, provided for purely illustrative and non-limiting purposes, in which FIG. 1 of said drawing is a schematic representation of an apparatus for measuring the flow-rate of different fluids present in a plurality of distinct multiphase streams, according to the present invention.

As schematically represented in FIG. 1 enclosed, the apparatus 1 is operatively associated with a plurality of main flow pipes 2 or multiphase stream lines, coming, for example, from respective extraction wells of hydrocarbons (not represented).

More specifically, the apparatus 1 represented is operatively associated with four main flow lines 2 destined for the transit of respective multiphase streams C coming from respective extraction wells.

The above-mentioned number of main flow pipes 2 is naturally an example of a grouping of pipes that can vary, depending on the specific cases, from a minimum of 2, to a maximum number N to be established, for example from 5 to 15.

According to the configuration illustrated in FIG. 1, the apparatus 1 is suitable for effecting the measurement of the flow-rate of different fluids, in particular, water, oil and gas, present in a plurality of distinct multiphase streams C, in transit, each through a respective main flow pipe 2.

As can be seen in FIG. 1, the apparatus 1 comprises at least one measurement unit 3 operatively associated with each main flow pipe 2.

According to the solution illustrated in FIG. 1, each measurement unit 3 coaxially intercepts a first portion 2a and a consecutive second portion 2b of the respective main flow pipe 2.

Each measurement unit 3 advantageously comprises a sampling device 4, in particular isokinetic, for the sampling of a predetermined quantity of a respective multiphase stream C in transit along the respective main flow pipe 2.

The isokinetic sampling device 4 has the function of collecting a flow rate P from the flow of the multiphase stream C in transit along the respective main flow pipe 2, diverting an aliquot P of the total flow-rate Q of said flow of the multiphase stream C, at the inlet of the respective main flow pipe 2.

First measuring- means 5, in particular a differential pressure measurer of the known type are situated in correspondence with the isokinetic sampling device 4, for measuring the pressure difference, after sampling, between the aliquot or sampled fraction P, collected, and the multiphase stream C or non-sampled fraction. This pressure difference must be zero to ensure that the sampling is isokinetic.

Each measurement unit 3 also comprises, along the respective main flow pipe 2 and downstream of the respective isokinetic sampling device 4, a flow restriction 6 which is such as to create the pressure drop necessary for effecting the required sampling.

Second measurement means 7 can be envisaged in correspondence with the flow restriction 6, advantageously a differential pressure measurer of the known type, suitable for measuring the pressure drop due to the passage of the flow when passing through the flow resticition 6.

Alternative known measurement methods, such as for example ultrasounds, vortex or volumetric measurers, can be used, when applicable, for determining the volumetric flow-rate.

Again with reference to FIG. 1, the apparatus 1 also comprises at least one separator device 8, preferably a compact separator, even more preferably having a high efficiency, operatively associated with the measurement unit 3 for separating the water, oil and gas phases present in the respective sampled fractions P collected by the respective sampling devices 4.

More specifically, the isokinetic sampling device 4 of each measuring unit 3 is in fluid communication with the above-mentioned separator device 8, to which the flow-rate of the respective fraction P collected is fed by means of a common feeding duct 9, to be separated into its liquid and gaseous components.

The liquid phases leave the bottom of the separator device 8 through at least one pipe 10, whereas the gaseous phase leaves the upper end of the separator device 8 through at least one pipe 11.

Two lower pipes can also be envisaged for the discharge of the liquid phases, each relating to a type of liquid present in the above-mentioned multiphase streams, i.e. water and oil.

Again with reference to FIG. 1, the apparatus 1 also comprises third measuring means 12, advantageously a measurer 12a of the liquid flow-rate of the known type and a measurer 12b of the gas flow-rate of the known type, operatively associated with the separator device 8 for respectively measuring the outgoing flow-rates of the different fluids present in the respective sampled fraction P.

The flow-rate meter 12a is advantageously operatively positioned between the separator device 8 and a joining connection 13 of the fluids separated. In this case, the pipe 10 is configured so as to feed the flow-rate of liquids inside the pipe 11 of the gaseous phase through the above-mentioned joining connection 13.

As can be seen in FIG. 1, the joining connection 13 of the liquid and gaseous phases is situated upstream of a respective coupling of the same in the tract 2b of the respective main flow pipe 2, downstream of the respective measurement unit 3.

A valve 14, which can be closed to effect non-continuous measurements, is advantageously operatively positioned between the joining connection 13 and the flowmeter of the liquids 12a of the third measuring means 12.

At least one level measurer 15, preferably of the differential type, is advantageously associated with the separator device 8.

Again with reference to FIG. 1, the pipe 11 relating to the gaseous phase is intercepted, upstream of the joining connection 13, by the gas flow-rate meter 12b of the third measurement means 12.

The apparatus also comprises regulation means 16, operatively positioned downstream of the joining connection 13 of the fluids separated at the outlet of the separator device 8, to control the flow-rate sampled by the respective sampling device 4 of the respective measuring unit 3.

Again with reference to FIG. 1, the apparatus 1 provides, for each main flow pipe 2 envisaged, a respective conveying duct 17 which is in fluid communication with the joining connection 13. Each conveying duct 17 is advantageously equipped with at least one valve 16a, preferably two, arranged in series, forming part of the regulation means 16 described above.

Each valve 16a is commutable between a closed condition, in which it blocks the respective conveying duct 17, and an open condition, in which it allows the passage of the fluids coming from said joining connection 13 towards the respective main flow pipe 2.

According to an advantageous aspect of the present invention, the apparatus 1 is also equipped with selection means 18 operatively interposed between each of the measuring units 3 envisaged and the separator device 8, to put the latter in fluid communication with the sampling device 4 of at least one measuring unit 3 selected.

More specifically, the selection means 18 are commutable between an exclusion condition, in which the sampling device 4 of each of the measuring units 3 is not in fluid communication with the separator device 8, and a selection condition, in which the sampling device 4 of at least one of the measuring units 3 is in fluid communication with the separator device 8, whereas the sampling device 4 of the other measuring units 3 is not in fluid communication with the separator device 8.

According to an alternative embodiment solution of the present invention, the flows collected from the main flow pipe 2 are not reinserted inside the same but in a common production line (not represented in the figure) into which the main flow pipes 2 converge.

According to this configuration, each main flow pipe 2 is in direct fluid communication with the common production line.

The joining connection 13 of the separator device 8 is also in direct fluid communication with the common production line, downstream of the connection between the main flow pipes 2 and the common production line 2.

One or more flow-interruption valves can be envisaged between the joining connection 13 of the separator device 8 and the common production line, which can be prevalently used for isolating the separator device 8 from the whole system when maintenance interventions are required.

The selection means 18 are advantageously operatively positioned along a tapping pipe 19 which extends between the sampling device 4 of each measuring unit 3 envisaged and the feeding duct 9 of the separator device 8.

In particular, the selection means 18 comprise, for each tapping pipe 19, at least one flow valve 18a positioned upstream of the respective coupling of the respective tapping pipe 19 in the feeding duct 9 of the separator device 8.

The apparatus 1 advantageously comprises data processing means (not represented as they are already known) suitable for receiving, through specific electric lines 20 and electric connectors 21, the data revealed by the first measuring means 5 of each measuring unit 3, the second measuring means 7 of each measuring unit 3, the third measuring means 12 of the separator device 8 and the regulation means 16 situated downstream of the joining connection 13.

The data processing means are also suitable for sending, through corresponding electric lines 20 and electric connectors 21, corresponding operative signals to the regulation means 16 to vary the flow-rate of the sampled fraction P in the sampling device 4 of each measuring unit 3.

The data processing means advantageously control, again through electric lines 20 and electric connectors 21, the selection means 18 between the exclusion condition and the selection condition in relation to the verifications to be effected in certain main flow pipes 2 and consequently in certain extraction wells.

Furthermore, upstream of the measurement unit 3 associated with each main flow pipe 2, the apparatus 1 can comprise at least one absolute pressure meter (not represented) and a temperature measurer (not illustrated), for respectively monitoring the pressure P and temperature T of the multiphase stream C which is flowing inside the respective main flow pipe 2.

An object of the present invention also relates to a method for measuring the flow-rates of each phase present in each of the streams C which flow in the above-mentioned main flow pipes 2.

The method according to the invention comprises a selection phase of the measuring unit 3 to be put in communication with the separator device 8.

More specifically, the selection phase is actuated by putting the sampling device 4 of the measuring unit 3 associated with the main flow pipe 2 on which the flow-rate measurement is to be effected, in fluid communication, by means of a suitable hydraulic connection, with the separator device 8, to separate the phases of the quantity of flow-rate P collected from the respective multiphase stream C.

The connection between the sampling device 4 selected and the separator device 8 is selectively effected excluding the connection between the sampling devices 4 applied to the other main flow lines 2 and the separator device 8.

The connection between the sampling device 4 selected and the separator device 8 is effected by commuting the respective valve 18a, hydraulically interposed between the separator device 8 and the corresponding sampling device 4, between the closed condition and open condition.

When the sampling device 4 to be put in communication with the separator device 8 has been selected, a sampling phase is then effected of a predetermined quantity of flow-rate of the respective multiphase stream C from an area section of the corresponding main flow pipe 2, in which there are substantially isokinetic conditions. In this way, the separator device 8 receives a fraction P of the multiphase stream C of a single flow pipe 2.

After the sampling, the sampled fraction P is suitably subjected to separation of the phases forming the respective multiphase stream in order to measure the flow-rate of each fluid separated, i.e. gas, water and oil.

The flow-rate of each phase separated in the separator device 8 is subsequently measured.

Once the flow-rate of each phase has been measured, the latter are rejoined in correspondence with the joining connection 13 to be finally introduced into the main flow pipe 2, from which they had been previously removed.

The apparatus and method according to the present invention solve the problems encountered in the known art and achieve important advantages.

First of all, the apparatus described above allows the cumbersome, heavy and costly selection manifold to be eliminated, through its substitution with a plurality of valves having limited dimensions. This substitution is possible as the fraction removed from the multiphase streams arriving from the respective extraction wells, corresponds to an aliquot of the same and varies in relation to the total flow-rate of the respective streams.

More specifically, as the fraction removed from each multiphase stream is established with respect to an aliquot, which preferably varies from $1/5$ to $1/10$ of an ideal predetermined maximum flow-rate, the aliquot removed varies in relation to the flow-rate of each stream.

For streams having a significant flow-rate close to or corresponding to the ideal predetermined maximum flow-rate, the aliquot removed corresponds to a value within the extremes indicated above.

For streams with limited flow-rates, the aliquot removed corresponds to the maximum flow-rate of the respective multiphase streams.

In this way, also without instruments for measuring the flow-rate of the single phases that cover the different ranges of values, the ratio between the scale bottom and lowest value revealable, i.e. the rangeability, can be broadened. The configuration of the apparatus described above therefore allows the flow-rates of the sampled fractions P to be subjected to the separation phase, to be significantly reduced. Consequently, both the selection means with the respective valves and the separator device with the measurement means and valves associated with this, are dimensioned for operating on overall flow-rates that are considerably reduced. Both the selection means and separator device therefore have reduced encumbrances and weights with respect to those of the known art which results in a reduction in the overall encumbrances and weights of the measurement apparatus.

It should also be pointed out that the apparatus described above allows an accurate measurement of the flow-rates of the phases under examination with significantly reduced overall costs, as the selection means consist of a valve for each measurement unit, whereas the separator device is dimensioned for the limited flow-rates to be examined.

The invention claimed is:

1. An apparatus for measuring the flow-rate of different fluids present in a plurality of distinct multiphase streams, in transit, each through a respective main flow pipe which does not form part of said apparatus, said apparatus comprising:
at least one measuring unit operatively associated with each main flow pipe, each measuring unit coaxially intercepting a first portion and a second portion, consecutive, of the respective main flow pipe and comprising: a sampling device, in particular isokinetic, for the sampling of a predetermined quantity of a respective multiphase stream, suitable for separating said multiphase stream into a sampled fraction and a non-sampled fraction; first measuring means of the differential pressure between the sampled fraction and non-sampled fraction situated downstream of the respective sampling device; a flow restriction having a reduced passage section with respect to the passage section of the respective flow pipe, situated downstream of the respective sampling device; second measuring means of the differential pressure operatively associated with the respective restriction;
a separator device operatively associated with said measuring unit for separating the phases of the respective fractions sampled and collected from the corresponding sampling devices;
selection means operatively interposed between said measuring units and said separator device for putting the latter in fluid communication with a sampling device of at least one of said measuring units, said selection means being commutable at least between an exclusion condition, in which the sampling device of each of the measuring units envisaged is not in fluid communication with said separator device, and a selection condition, in which at least one of the measuring units envisaged, is in fluid communication with said separator device, whereas the sampling device of the other remaining measuring units is not in fluid communication with said separator device;
third measuring means operatively associated with said separator device for measuring the outgoing flow-rates of the different fluids present in the respective sampled fraction, said third measuring means being operatively arranged between said separator device and a joining connection of the fluids separated;
regulation means, operatively positioned downstream of said joining connection, to control the flow-rate sampled by the respective sampling device of the respective measuring unit in fluid communication with said separator device;
data processing means suitable for receiving and processing the data collected from said first and second measuring means of each measuring unit, from said third measuring means of said separator device and from said regulation means situated downstream of said joining connection, said data processing means being suitable for sending operative signals to said regulation means for varying the flow-rate of the sampled fraction in each sampling device of each measuring unit, said data processing means commanding the selection means between the exclusion condition and the selection condition.

2. The apparatus according to claim 1, comprising: at least one feeding duct of said fractions sampled by the sampling device of each measuring unit, interposed between said separator device and said measuring unit; a tapping pipe for each measuring unit extending from the sampling device of the respective measuring unit and in fluid communication with said separator device through said feeding duct, said selection means comprising, for each measuring unit, at least one flow valve operatively situated along the respective tapping pipe upstream of said feeding duct of said separator device.

3. The apparatus according to claim 1, comprising, for each main flow pipe envisaged, a respective conveying duct in fluid communication with said joining connection, each conveying duct being equipped with at least one valve commutable between a closed condition, in which it blocks the respective conveying duct, and an open condition, in which it allows the passage of the fluids coming from said joining connection towards the respective main flow pipe.

4. The apparatus according to claim 1, wherein the sampling device of each measuring unit is suitable for collecting from each multiphase stream an aliquot, variable from $1/5$ to $1/10$ of a predetermined ideal maximum flow-rate, whereby the aliquot collected varies in relation to the flow-rate of each multiphase stream.

5. A method for measuring the flow-rates of each phase in a plurality of distinct multiphase streams which are flowing in respective and different main flow pipes, said method comprising:
collecting a predetermined quantity of flow-rate of a respective multiphase stream from a section of an area of one of said main flow pipes, in which substantially isokinetic conditions are verified, the collection of said quantity of flow-rate being effected by means of a respective isokinetic sampling device;
putting the respective sampling device in fluid communication, by means of a hydraulic connection, with a separator device for separating the phases of the quantity of flow-rate collected, the connection between the sampling device selected and the separator device, being effected excluding the hydraulic connection between the sampling device applied to the other main flow pipes and the separator device;
measuring the flow-rate of each phase separated in the separator device;
joining the phases separated after measuring the flow-rate of the same;
introducing the joined phases into the respective main flow pipe;
the connection between the sampling device selected and the separator device being effected by commuting a respective valve, hydraulically interposed between said separator device and the sampling device associated with the respective main flow line.

6. The method according to claim 5, wherein the sampling phase of a predetermined quantity of flow-rate of a respective multiphase stream comprises a phase for collecting from each multiphase stream an aliquot, variable from $1/5$ to $1/10$ of a predetermined ideal maximum flow-rate, whereby the aliquot collected varies in relation to the flow-rate of each multiphase stream.

* * * * *